United States Patent [19]

Claremon et al.

[11] Patent Number: 5,439,914
[45] Date of Patent: Aug. 8, 1995

[54] SPIROCYCLES

[75] Inventors: David A. Claremon, Maple Glen; Gerald S. Ponticello, Lansdale; Harold G. Selnick, Ambler, all of Pa.

[73] Assignee: Merck & Co., Inc., Rahway, N.J.

[21] Appl. No.: 198,940

[22] Filed: Feb. 18, 1994

[51] Int. Cl.[6] .................. A61K 31/445; C07D 491/107
[52] U.S. Cl. ...................................... 514/278; 546/17
[58] Field of Search ........................... 546/17; 514/278

[56]  References Cited

U.S. PATENT DOCUMENTS

| | | | |
|---|---|---|---|
| 3,649,635 | 3/1972 | Von Strandtmann et al. | 260/287 R |
| 3,686,186 | 8/1972 | Houlihan et al. | 260/293.58 |
| 3,980,655 | 9/1976 | Kunstmann et al. | 260/288 A |
| 4,166,119 | 8/1979 | Effland et al. | 546/17 |
| 4,353,900 | 10/1982 | Clark | 544/71 |
| 4,420,485 | 12/1983 | Davis et al. | 548/408 |
| 4,544,654 | 10/1985 | Davey et al. | 514/210 |

(List continued on next page.)

FOREIGN PATENT DOCUMENTS

| | | |
|---|---|---|
| 0121972 | 10/1984 | European Pat. Off. |
| 0235752 | 9/1987 | European Pat. Off. |
| 0281254 | 9/1988 | European Pat. Off. |
| 0284384 | 9/1988 | European Pat. Off. |
| 0285284 | 10/1988 | European Pat. Off. |

(List continued on next page.)

OTHER PUBLICATIONS

Rice et al, Chem Abs 65, 16935 (1966).
Bauer, et al., J. Med. Chem., 19, (1976) pp. 1315–1324.
(List continued on next page.)

*Primary Examiner*—Mark L. Berch
*Attorney, Agent, or Firm*—Francis P. Bigley; Mark R. Daniel; Joseph F. DiPrima

[57]  ABSTRACT

Compounds of the general structural formula:

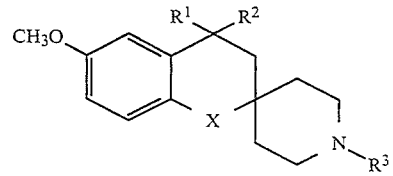

or a pharmaceutically acceptable salt, hydrate or crystal form thereof, wherein;

X is O or $CH_2$
$R^1$ is H if $R^2$ is not H or if $R^2$ is H then $R^1$ is

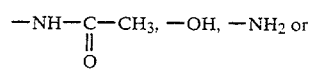

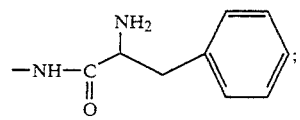

$R^2$ is —H if $R^1$ is not H or if $R^1$ is H then $R^2$ is;

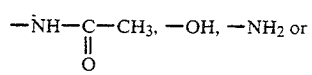

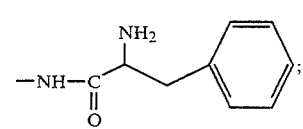

and
$R^3$ is

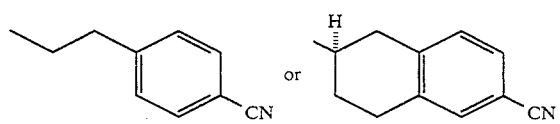

are Class III antiarrhythmic agents.

9 Claims, No Drawings

U.S. PATENT DOCUMENTS

| | | | |
|---|---|---|---|
| 4,629,739 | 12/1986 | Davey et al. | 514/210 |
| 4,650,798 | 3/1987 | Minami et al. | 544/230 |
| 4,788,196 | 11/1988 | Cross et al. | 514/252 |
| 4,797,401 | 1/1989 | Kemp et al. | 544/392 |
| 4,804,662 | 2/1989 | Nickisch et al. | 514/252 |
| 4,806,536 | 2/1989 | Cross et al. | 544/360 |
| 4,806,555 | 2/1989 | Lunsford | 514/652 |
| 4,810,792 | 3/1989 | Kosley, Jr. | 546/216 |
| 4,845,099 | 4/1989 | Ruger et al. | 514/253 |
| 5,091,387 | 2/1992 | Evans | 546/17 |
| 5,206,240 | 4/1993 | Baldwin et al. | 514/231.5 |
| 5,219,860 | 6/1993 | Chambers | 546/17 |
| 5,382,587 | 1/1995 | Baldwin | 514/278 |

FOREIGN PATENT DOCUMENTS

| | | |
|---|---|---|
| 0285323 | 10/1988 | European Pat. Off. . |
| 0286277 | 10/1988 | European Pat. Off. . |
| 0286278 | 10/1988 | European Pat. Off. . |
| 0300908 | 1/1989 | European Pat. Off. . |
| 0307121 | 3/1989 | European Pat. Off. . |
| 0397121 | 11/1990 | European Pat. Off. . |

OTHER PUBLICATIONS

J. M. Elliott, et al., J. Med. Chem. (1992), 35, pp. 3973–3976.

Iorio, et al., II Farmaco–Ed Sci., 32, (1977) pp. 212–219.

Parham, et al., J. Org. Chem., 41, (1976) pp. 2628–2633.

SPIROCYCLES

BACKGROUND OF THE INVENTION

Arrhythmias often occur as complications to cardiac diseases such as myocardial infarction and heart failure. In a serious case, arrhythmias give rise to a ventricular fibrillation and can cause sudden death.

Though various antiarrythmic agents are now available on the market, those having both satisfactory effects and high safety, have not been obtained. For example, antiarrythmic agents of Class I according to the classification of Vaughan-Williams which cause a selective inhibition of the maximum velocity of the upstroke of the action potential ($V_{max}$) are inadequate for preventing ventricular fibrillation. In addition, they have problems regarding safety, namely, they cause a depression of the myocardial contractility and have a tendency to induce arrythmias due to an inhibition of the impulse conduction. Beta-adrenoceptor blockers and calcium antagonists which belong to Class II and IV respectively, have a defect that their effects are either limited to a certain type of arrhythmia or are contraindicated because of their cardiac depressant properties in certain patients with cardiovascular disease. Their safety, however, is higher than that of the antiarrhythmic agents of Class I.

Antiarrythmic agents of Class III are drugs which cause a selective prolongation of the duration of the action potential without a significant depression of the $V_{max}$. Drugs in this class are limited. Examples such as sotalol and amiodarone have been shown to possess Class III properties. Sotalol also possesses Class II effects which may cause cardiac depression and be contraindicated in certain susceptible patients. Also, amiodarone is severely limited by side effects. Drugs of this class are expected to be effective in preventing ventricular fibrillations. Pure Class III agents, by definition, are not considered to cause myocardial depression or an induction of arrhythmias due to the inhibition of the action potential conduction as seen with Class I antiarrhythmic agents.

A number of antiarrhythmic agents have been reported in the literature, such as those disclosed in:
(1) EP 397,121-A, (2) EP 300,908-A, (3) EP 307,121,
(4) U.S. Pat. No. 4,629,739, (5) U.S. Pat. No. 4,544,654, (6) U.S. Pat. No. 4,788,196,
(7) EP application 88302597.5,
(8) EP application 88302598.3,
(9) EP application 88302270.9,
(10) EP application 88302600.7,
(11) EP application 88302599.1,
(12) EP application 88300962.3,
(13) EP application 235,752,
(14) DE 3633977-A1,
(15) U.S. Pat. No. 4,804,662,
(16) U.S. Pat. No. 4,797,401,
(17) U.S. Pat. No. 4,806,555,
(18) U.S. Pat. No. 4,806,536.

Compounds of similar structure are found in Japanese patent publication 88-63533-B of Daiichi Pharmaceutical Co.; *J. Med. Chem.*, 19, 1315 (1976) by Bauer et al; Iorio et al in *Il Farinaco-Ed Sci.*, 32, 212–219 (1977): Houlihan et al, U.S. Pat. No. 3,686,186; Davis et al, U.S. Pat. No. 4,420,485; Kealey, U.S. Pat. No. 4,810,792; Parham et al, *J. Org. Chem.*, 41, 2629 (1976). None of the compounds disclosed in the foregoing references are alleged to have antiarrhythmic activity.

Exemplary of the newest form of antiarrhythmic compounds are those disclosed in U.S. Ser. No. 07/447,950, filed on Dec. 8, 1989, ABN U.S. Ser. No. 07/998,321, filed Dec. 30, 1992. These specifications are hereby expressly incorporated by reference.

Now with the present invention, there is provided as antiarrhythmic agents new compounds with an increased degree of activity and longer biological duration. That is, the compounds of the instant invention are Class III antiarrhythmic agents useful in the treatment of ventricular or supraventricular arrhythmias. The compounds can be administered either orally or intravenously. These compounds exhibit a longer duration of action than any known similar compounds and are therefore a significant advancement over other compounds in this class of pharmaceuticals.

SUMMARY OF THE INVENTION

This invention is concerned with novel compounds of the general structural formula:

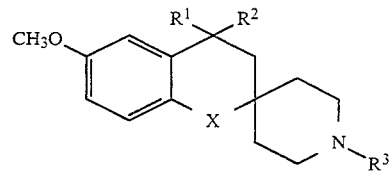

or a pharmaceutically acceptable salt, hydrate or crystal form thereof, wherein;
X is O or $CH_2$
$R^1$ is H if $R^2$ is not H or if $R^2$ is H then $R^1$ is

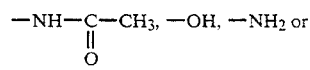

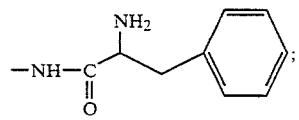

$R^2$ is —H if $R^1$ is not H or if $R^1$ is H then $R^2$ is;

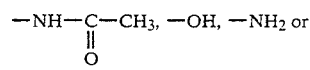

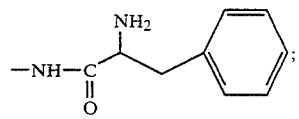

and
$R^3$ is

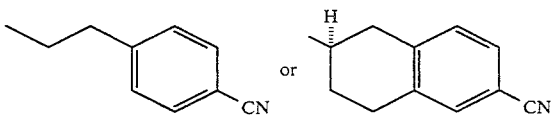

are Class III antiarrhythmic agents.

The invention is also concerned with pharmaceutical formulations comprising one or more of the novel compounds as active ingredient, either alone or in combination with one or more of a Class I, Class II or Class IV antiarrhythmic agent.

The invention is also concerned with a method of treatment of arrhythmia and impaired cardiac pump functions with the above-described novel compounds and formulations thereof.

The invention is further concerned with processes for preparing the novel compounds.

The invention is also concerned with providing a method of treatment for arrhythmia using compounds which exhibit a longer during of action.

DETAILED DESCRIPTION OF THE INVENTION

Compounds of the general structural formula: Compounds of the general structural formula:

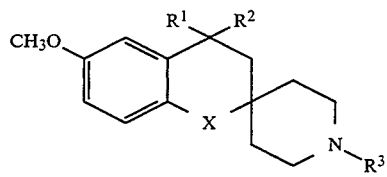

or a pharmaceutically acceptable salt, hydrate or crystal form thereof, wherein;

$X$ is O or $CH_2$ $R^1$ is H if $R^2$ is not H or if $R^2$ is H then $R^1$ is

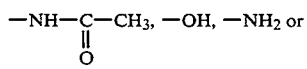

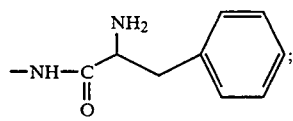

$R^2$ is —H if $R^1$ is not H or if $R^1$ is H then $R^2$ is;

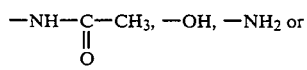

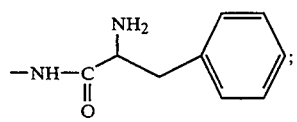

and
$R^3$ is

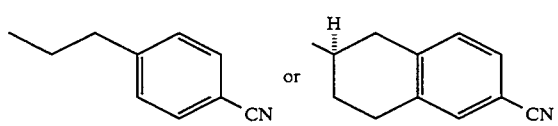

are Class III antiarrhythmic agents.

Preferred compounds include:

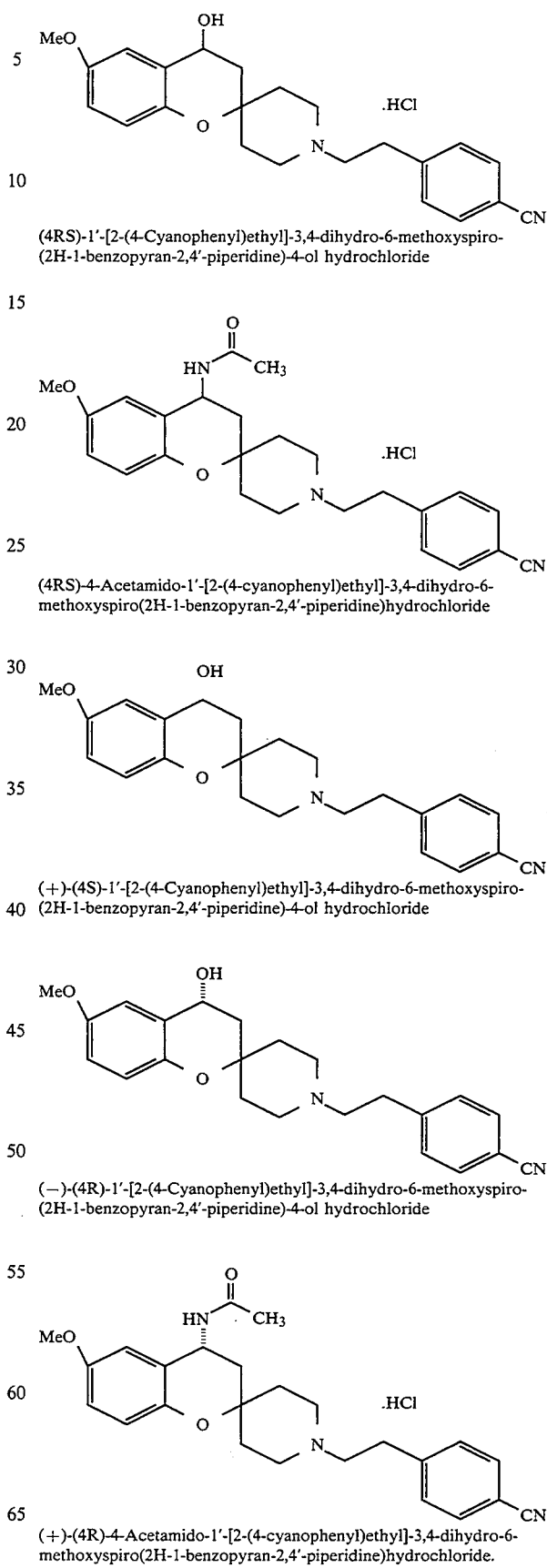

(4RS)-1'-[2-(4-Cyanophenyl)ethyl]-3,4-dihydro-6-methoxyspiro-(2H-1-benzopyran-2,4'-piperidine)-4-ol hydrochloride (4RS)-4-Acetamido-1'-[2-(4-cyanophenyl)ethyl]-3,4-dihydro-6-methoxyspiro(2H-1-benzopyran-2,4'-piperidine)hydrochloride (+)-(4S)-1'-[2-(4-Cyanophenyl)ethyl]-3,4-dihydro-6-methoxyspiro-(2H-1-benzopyran-2,4'-piperidine)-4-ol hydrochloride (−)-(4R)-1'-[2-(4-Cyanophenyl)ethyl]-3,4-dihydro-6-methoxyspiro-(2H-1-benzopyran-2,4'-piperidine)-4-ol hydrochloride (+)-(4R)-4-Acetamido-1'-[2-(4-cyanophenyl)ethyl]-3,4-dihydro-6-methoxyspiro(2H-1-benzopyran-2,4'-piperidine)hydrochloride.

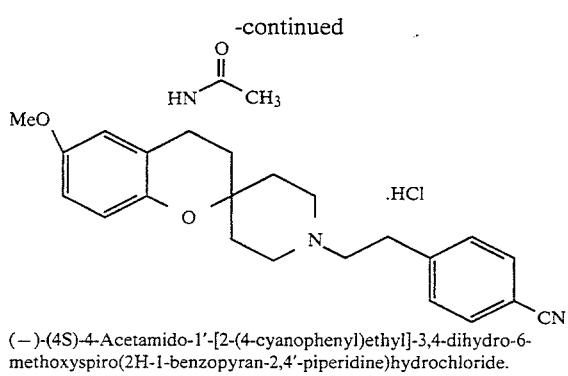

(−)-(4S)-4-Acetamido-1′-[2-(4-cyanophenyl)ethyl]-3,4-dihydro-6-methoxyspiro(2H-1-benzopyran-2,4′-piperidine)hydrochloride.

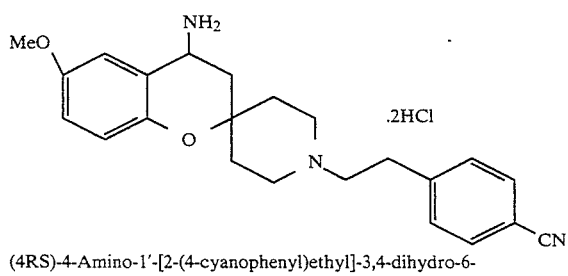

(4RS)-4-Amino-1′-[2-(4-cyanophenyl)ethyl]-3,4-dihydro-6-methoxyspiro(2H-1-benzopyran-2,4′-piperidine)hydrochloride

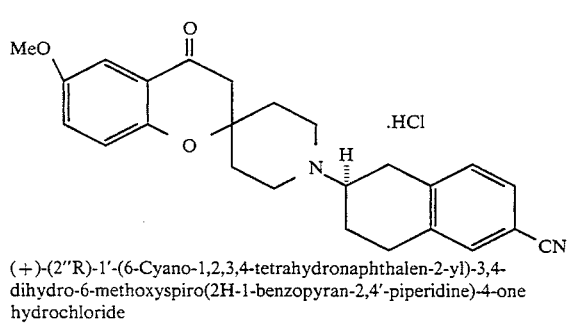

(+)-(2″R)-1′-(6-Cyano-1,2,3,4-tetrahydronaphthalen-2-yl)-3,4-dihydro-6-methoxyspiro(2H-1-benzopyran-2,4′-piperidine)-4-one hydrochloride

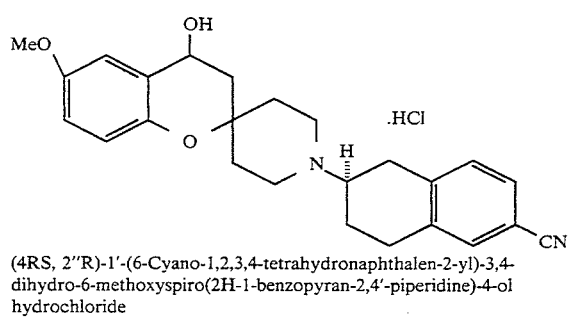

(4RS, 2″R)-1′-(6-Cyano-1,2,3,4-tetrahydronaphthalen-2-yl)-3,4-dihydro-6-methoxyspiro(2H-1-benzopyran-2,4′-piperidine)-4-ol hydrochloride

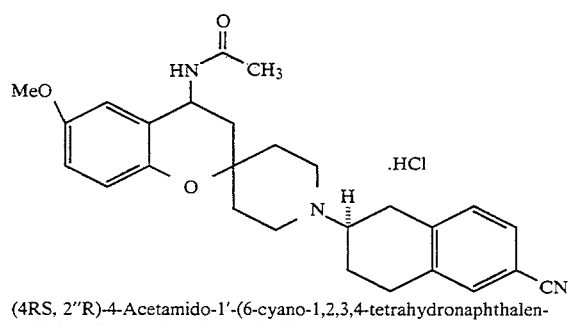

(4RS, 2″R)-4-Acetamido-1′-(6-cyano-1,2,3,4-tetrahydronaphthalen-2-yl)-3,4-dihydro-6-methoxyspiro(2H-1-benzopyran-2,4′-piperidine) hydrochloride and pharmaceutically acceptable salts, hydrates and crystal forms thereof.

Also included within the scope of the present invention are the non-toxic pharmaceutically acceptable salts of the novel compounds. Acid addition salts are formed by mixing a solution of the compound with a solution of a pharmaceutically acceptable non-toxic acid such as hydrochloric acid, fumaric acid, maleic acid, methanesulfonic acid, isethionic acid, succinic acid, acetic acid, citric acid, tartaric acid, phosphoric acid, or the like. Also included within the scope of this invention are N-oxides.

Also included within the scope of this invention are diastereomers and enantiomers of the novel compounds and mixtures thereof.

The novel compounds of the present invention, have the pharmacological properties required for the antiarrhythmic agents of Class III, namely the prolongation of the myocardial action potential in vitro, without a significant depression of the $V_{max}$, and the prolongation of $QT_c$-interval in anesthetized dogs.

In addition these compounds also have the pharmacological properties required for the antiarrhythmic agents of Class III. Moreover, the members of both groups of compounds in general are much more potent than the reference drug, sotalol.

These compounds are effective in treating and preventing all types of arrhythmias including ventricular and atrial (supraventricular) arrhythmias. The compounds of the present invention are especially useful to control reentrant arrhythmias and prevent sudden death due to the ventricular fibrillation. These compounds are also effective in treating and preventing impaired cardiac pump functions.

In the novel method of this invention of treating arrhythmia, one of the compounds or pharmaceutically acceptable salt thereof, is administered in an amount ranging from about 0.0001 to about 20 mg per kg of body weight per day, preferably from about 0.001 to about 10 mg per kg of body weight per day in a single dose or in 2 to 4 divided doses.

These compounds can be administered as the sole active ingredient or in combination with other antiarrhythmic agents or other cardiovascular agents, such as a Class I, Class II or Class IV antiarrhythmic agent.

By Class I antiarrhythmic agents is meant those agents which provide for sodium channel blockade, including those compounds which exert a membrane stabilizing effect. Exemplary of this class of compounds are quinidine, procainamide, disopymmide, lidocane, tocaninide, flecainide and propafenone. By Class II antiarrhythmic compounds is meant those agents which block sympathetic activity. Exemplary of this class of compounds are propranolol and acebutolol. By Class III antiarrhythmic agents is meant those compounds which prolong the effective refractory period without altering the resting membrane potential or rate of depolarization. In addition to the novel compounds of this invention, compounds such as amiodarone, bretylium and sotalol are considered to be in this class. Class IV antiarrhythmic agents are effective in calcium channel blockade.

These compounds, or pharmaceutically acceptable salts thereof, in the described dosages, are administered orally, intraperitoneally, subcutaneously, intramuscularly, transdermally, sublingually or intravenously. They are preferably administered intravenously or orally, for example in the form of tablets, troches, capsules, elixirs, suspensions, syrups, wafers, chewing gum, controlled release delivery systems or the like prepared by art recognized procedures. The amount of active compound in such therapeutically useful compositions or preparations is such that a suitable dosage will be obtained.

EXAMPLES

The following examples are given for the purpose of illustrating the present invention and shall not be construed as being limitations on the scope or spirit of the instant invention.

The novel processes of this invention can be exemplified by the following Reaction Schemes and the examples that accompany each scheme:

SCHEME I

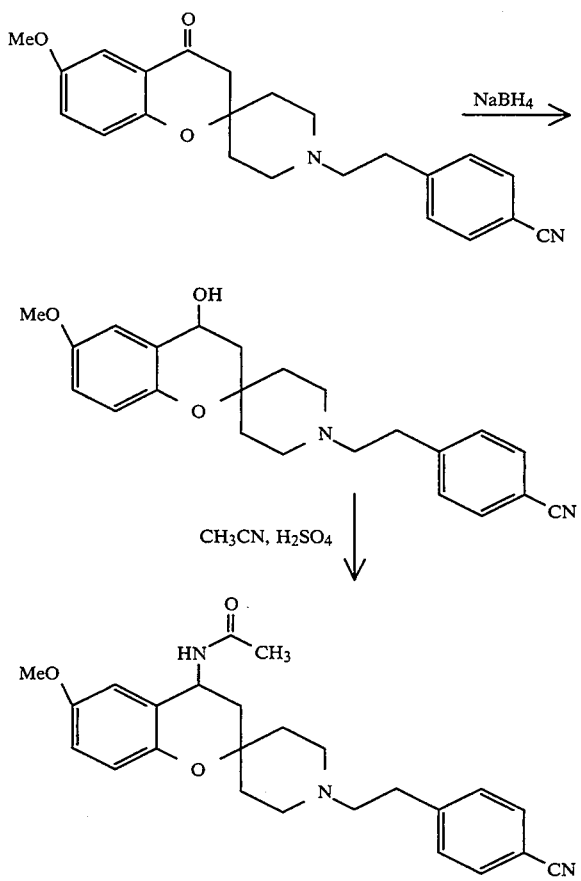

Scheme 1

EXAMPLE 1

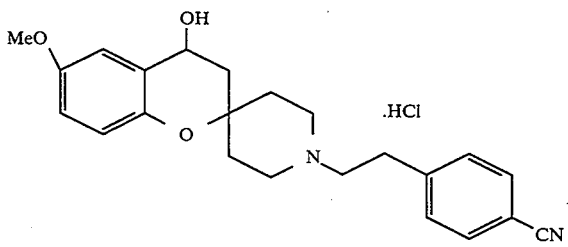

(4RS)-1'-[2-(4-Cyanophenyl)ethyl]-3,4-dihydro-6-methoxyspiro(2H-1-benzopyran -2,4'-piperidine)-4-ol hydrochloride A solution of 1'-[2-(4-cyanophenyl)ethyl]-3,4-dihydro-6-methoxyspiro(2H-1-benzopyran -2,4'-piperidine)-4-one hydrochloride (412 mg, 1 mmol) in ethanol (25 ml) at room temperature was treated with sodium borohydride (0.10 g, 2.65 mmol) and stirred at room temperature for 1 h. The reaction was poured into saturated aqueous sodium bicarbonate and extracted with ethyl acetate. The combined extracts were dried over anhydrous magnesium sulfate, filtered, and concentrated at reduced pressure. The residue was chromatographed on silica gel with chloroform/methanol (95:5) as eluent to give 0.322 g of free base. The material thus obtained was treated with excess ethanolic HCl and the product crystallized from ethanol to give the hydrochloride (215 mg, 52%), m.p. 224°–226 ° C.

Elementary analysis for $C_{23}H_{26}N_2O_3 \cdot HCl1.0 \cdot .1EtOH \cdot 0.35H_2O$:

Calculated; C 65.43; H 6.70; N 6.58%. Found; C 65.44; H 6.60; N 6.43%.

EXAMPLE 2

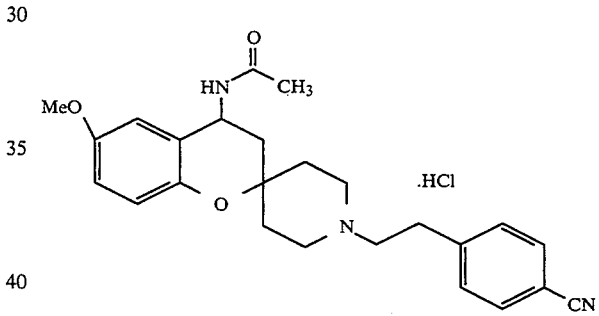

(4RS)-4-Acetamido-1'-[2-(4-cyanophenyl)ethyl]-3,4-dihydro-6-methoxyspiro(2H-1-benzopyran-2,4'-piperidine)hydrochloride A solution of (4RS)-1'-[2-(4-cyanophenyl)ethyl]-3,4-dihydro-6-methoxyspiro(2H-1-benzopyran-2,4'-piperidine)-4-ol (600 mg, 1.6 mmol) in acetonitrile at room temperature was treated with concentrated sulfuric acid (0.25 ml) and the reaction stirred at room temperature for 2 h. The reaction was poured into saturated aqueous sodium bicarbonate (300 ml) and extracted with ethyl acetate (3×100 ml). The combined extracts were dried over anhydrous magnesium sulfate, filtered, and concentrated at reduced pressure. The residue was chromatographed on silica gel with chloroform/methanol (97:3 to 95:5) as eluent to give 0.310 g of free base. This material was treated with excess ethanolic HCl and the product crystallized from ethanol to give the hydrochloride (195 mg, 27%), m.p. 250° C.

Elementary analysis for $C_{25}H_{29}N_3O_3 \cdot HCl \cdot 0.05EtOH \cdot 1.10H_2O$:

Calculated; C63.05; H 6.85; N 8.79%. Found; C 62.72; H 6.46; N 8.77%.

SCHEME II

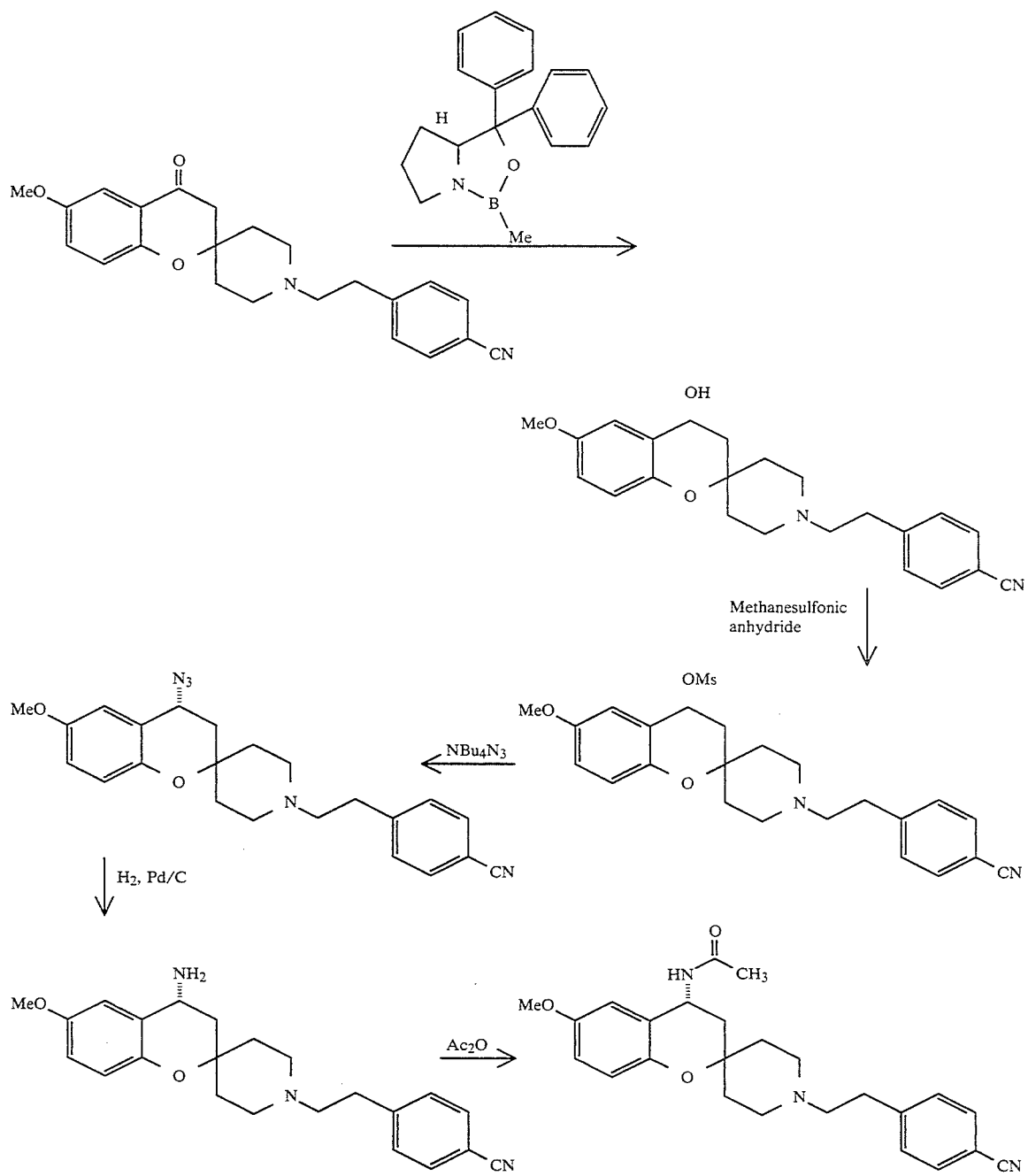

EXAMPLE 3

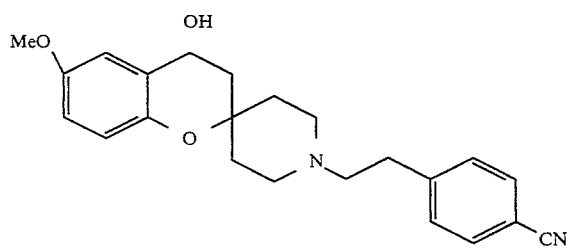

(+)-(4S)-1'-[2-(4-Cyanophenyl)ethyl]-3,4-dihydro-6-methoxyspiro(2H-1-benzopyran-2,4'-piperidine)-4-ol hydrochloride A solution of 1'-[2-(4-cyanophenyl)ethyl]-3,4-dihydro-6-methoxyspiro(2H-1-benzopyran-2,4'-piperidine)-4-one (2.6 g, 6.86 mmol) in methylene chloride (50 ml) at −20° C. was treated with (R)-tetrahydro-1-methyl-3,3-diphenyl-1H,3H-pyrrolo[1,2-c][1,2,3]-oxazaboroleborane complex (0.10 g, 2.65 mmol) and warmed slowly to 0° C. over 1 h. Methanol (10 mL) was added and the reaction mixture was concentrated in vacuo. Methanol (50 mL) was added and the reaction concentrated again. The residue was dissolved in methylene chloride (40 mL) and cooled to 0° C. Acetic anhydride was added (948 mg, 9.2 mmole) and the reaction warmed slowly to room temperature over 1 hour. The reaction was poured into saturated aqueous sodium bicarbonate (300 ml) and extracted with ethyl acetate (3×150 ml). The combined extracts were dried over anhydrous magnesium sulfate, filtered, and concentrated at reduced pressure. The residue was chromatographed on silica gel with chloroform/methanol (98:2 to 90:10) as eluent to give 1.81 g of free base. [α]$_D$= +5.75 (c=1.18, MeOH); $^1$H NMR CDCl$_3$ δ7.58 (d, J=8 Hz, 1 H), 7.32 (d, J =8 Hz, 1 H), 6.99 (s, 1H), 6.79 (s, 2H), 4.84 (t, J=6 Hz, 1 H), 3.78 (s, 3H), 2.95–2.85 (m, 2 H), 2.85–2.65 (m, 4 H), 2.65–2.40 (m, 2 H), 2.15 (dd, J=6, 13 Hz, 1H), 2.05–1.95 (m, 1H), 1.95–1.65 (m, 4 H)

EXAMPLE 4

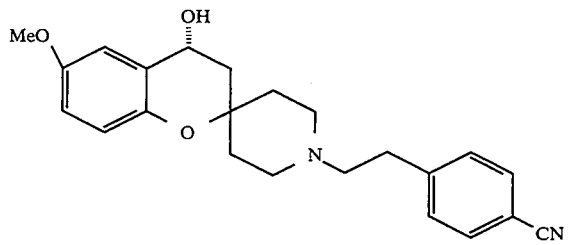

(−)-(4R)-1'-[2-(4-Cyanophenyl)ethyl]-3,4-dihydro-6-methoxyspiro(2H-1-benzopyran -2,4'-piperidine)-4-ol hydrochloride Prepared in a manner substantially as described above except using (S)-tetrahydro-1-methyl-3,3-diphenyl-1H,3H-pyrrolo[1,2,c][1,2,3]-oxazaborole-borane complex as the chiral reducing agent. [α]$_D$= −5.75 (c=1.2, MeOH); $^1$H NMR CDCl$_3$δ7.58 (d, J=8 Hz, 1 H), 7.32 (d, J=8 Hz, 1 H), 6.99 (s, 1H), 6.79 (s, 2H), 4.84 (t, J=6 Hz, 1 H), 3.78 (s, 3H), 2.95–2.85 (m, 2 H), 2.85–2.65 (m, 4 H), 2.65–2.40 (m, 2 H), 2.15 (dd, J=6, 13 Hz, 1H), 2.05–1.95 (m, 1H), 1.95–1.65 (m, 4 H)

EXAMPLE 5

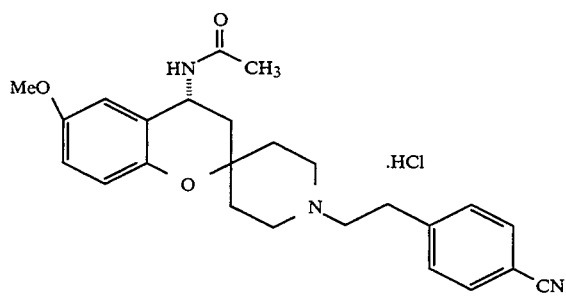

(+)-(4R)-4-Acetamido-1'-[2-(4-cyanophenyl)ethyl]-3,4-dihydro-6-methoxyspiro(2H -1-benzopyran-2,4'-piperidine) hydrochloride.

A solution of (+)-(4S)-1'-[2-(4-Cyanophenyl)ethyl]-3,4-dihydro-6-methoxyspiro(2H-1-benzopyran-2,4'-piperidine )-4ol (700 mg, 1.85 mmole) in methylene chloride (10 mL) at −78° C. was treated with a solution of methanesulfonic anhydride (696 mg, 4 mmole) in methylene chloride (2 mL) added via syringe. The reaction was stirred at −78° C. for 3 minutes and a solution of tetra-n-butylammonium azide (2.1 g, 7.4 mmole) in methylene chloride (4 mL) was added. The reaction was allowed to warm to room temperature over 1 hr. The reaction was poured into saturated aqueous sodium bicarbonate (100 ml) and extracted with ethyl acetate (3×100 ml). The combined extracts were dried over anhydrous magnesium sulfate, filtered, and concentrated at reduced pressure. The residue was chromatographed on silica gel with chloroform/methanol (98:2) as eluent to give 0.580 g of azide free base. This material was dissolved in ethanol (10 mL) and added to a suspension of 10% Pd/C in ethanol (10 ml). Hydrogen gas was bubbled into the reaction for 0.5 hour. The catalyst was filtered off and rinsed with ethyl acetate (@25 mL). The filtrate was concentrated at reduced pressure to give 460 mg of crude amine free base. The amine was dissolved in methylene chloride (20 mL) and treated with acetic anhydride (150 mg, 138 μL, 1.5 mmole).The reaction was stirred at room temperature for 15 minutes. The reaction was poured into saturated aqueous sodium bicarbonate (100 ml) and extracted with ethyl acetate (3×100 ml). The combined extracts were dried over anhydrous magnesium sulfate, filtered, and concentrated at reduced pressure. The residue was chromatographed on silica gel with chloroform/methanol (95:5 to 90:10) as eluent to give 0.350 g of amide free base. This material was treated with excess ethanolic HCl and the product as crystallized from 2-propanol to remove racemic material which selectively crystallized. After collecting three crops, the filtrate was concentrated to dryness and the residue crystallized from acetonitrile to give the hydrochloride. 152 mg, mp. 255°–257° C. Elementary analysis for C$_{25}$H$_{29}$N$_3$O$_3$.HCl.0.65 H$_2$O:

Calculated; C 64.20; H 6.75; N 8.99%. Found; C 64.14; H 6.51; N 8.79%. [α]$_D$= +56.6 (C=0.26, MeOH)

EXAMPLE 6

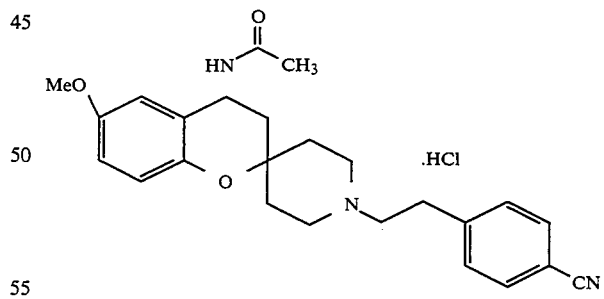

(−)-(4S)-4-Acetamido-1'-[2-(4-cyanophenyl)ethyl]-3,4-dihydro-6-methoxyspiro (2H-1-benzopyran-2,4'-piperidine) hydrochloride.

Prepared in a manner substantially as described above except using (−)-(4R)-1'-[2-(4-Cyanophenyl)ethyl]-3,4-dihydro-6-methoxyspiro-(2H-1-benzopyran-2,4'-piperidine )-4-ol as starting material mp 260°–263° C.

Elementary analysis for C$_{25}$H$_{29}$N$_3$O$_3$.HCl.0.3 H$_2$O:

Calculated; C 65.07; H 6.69; N 9.11%. Found; C 65.04; H 6.59; N 9.16%.

[α]$_D$= −58.1 (C=0.43, MeOH)

SCHEME III
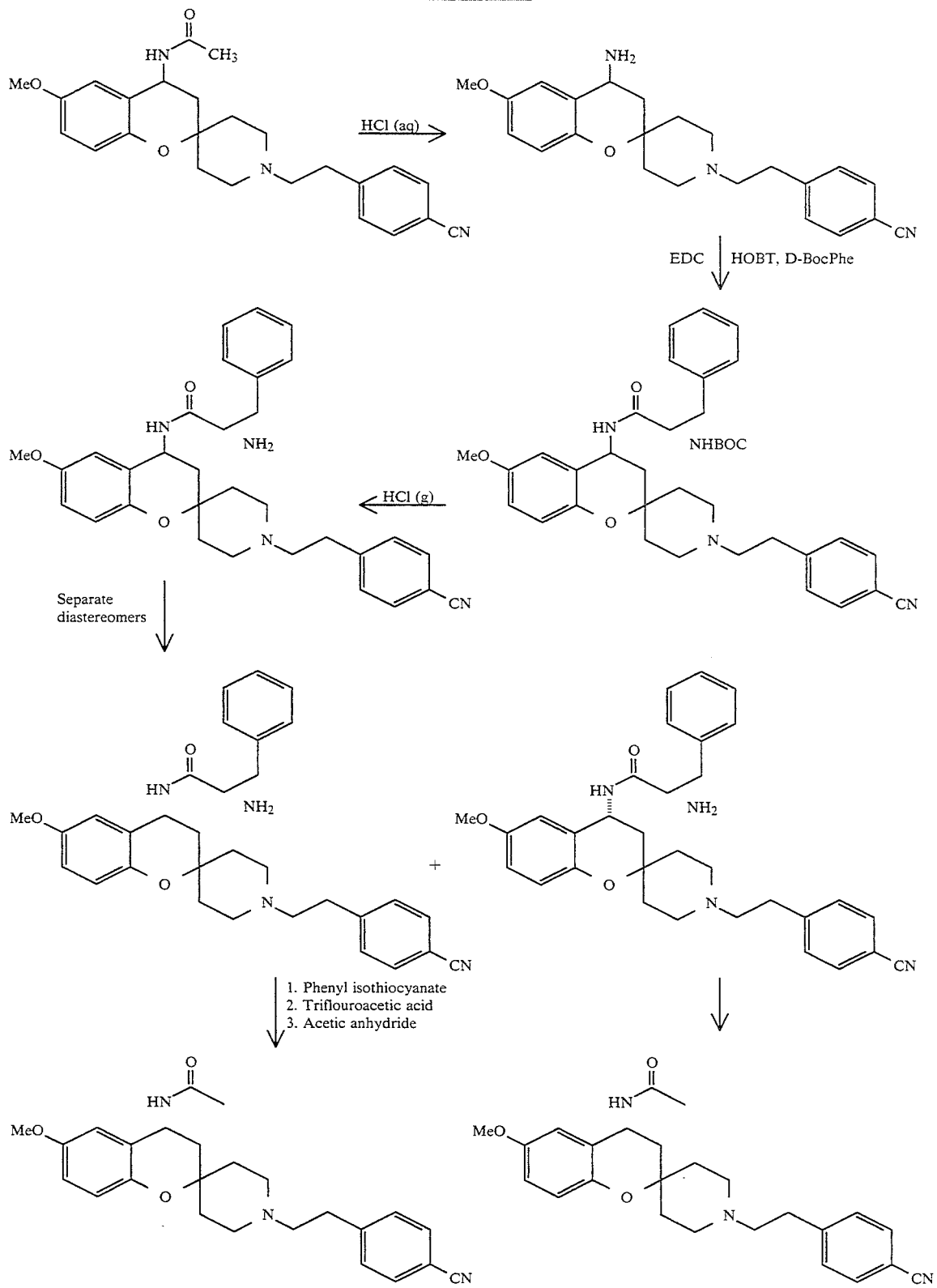
Scheme 3
Alternative resolution of 4-Acetamido-1'-[2-(4-cyanophenyl)ethyl]-3,4-dihydro-6-methoxyspiro (2H1-benzopyran-2,4'-piperidine) hydrochloride

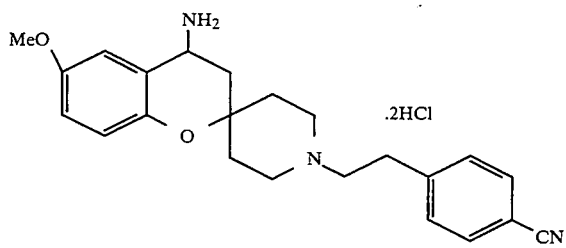

(4RS)-4-Amino-1'-[2-(4-cyanophenyl)ethyl]-3,4-dihydro-6-methoxyspiro(2H-1-benzopyran-2,4'-piperidine) hydrochloride A solution of 4-Acetamido-1'-[2-(4-cyanophenyl)ethyl]-3,4-dihydro-6-methoxyspiro (2H-1-benzopyran-2,4'-piperidine) (1 g, 2.38 mmole) in ethanol(10 mL) and 2 N HCl (60 mL) was heated to reflux for 16 hr. The reaction was cooled and poured into a mixture of 1 N NaOH (70 mL) and saturated sodiumbicarbonate (300 mL). The aqueous mixture was extracted with ethyl acetate (3×200 mL). The combined organics were dried over anhydrous magnesium sulfate, filtered and concentrated at reduced pressure to give 906 mg of the product as the free base. A sample (100 mg) was treated with excess ethanolic HCl and crystallized from isopropyl alcohol to give 81 mg of the dihydrochloride. mp 260°–263° C. Elementary analysis for $C_{23}H_{27}N_3O_2 \cdot 2HCl \cdot 0.75\ H_2O$: Calculated; C 59.55; H 6.84; N 8.77%. Found; C 59.55; H 6.50; N 8.75%.

EXAMPLE 8

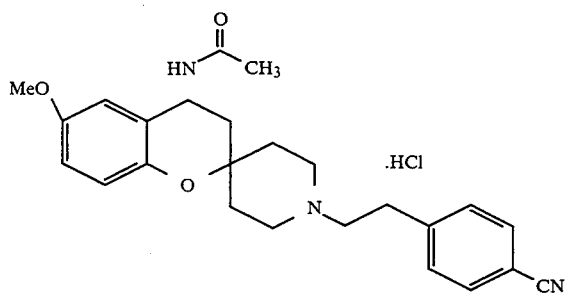

(−)-(4S)-4-Acetamido-1'-[2-(4-cyanophenyl)ethyl]-3,4-dihydro-6-methoxyspiro(2H -1-benzopyran-2,4'-piperidine) hydrochloride.

A solution of racemic 4-Amino-1'-[2-(4-cyanophenyl)ethyl]-3,4-dihydro-6-methoxyspiro(2H -1-benzopyran-2,4'-piperidine) (377.5 mg, 1 mmole) in DMF (5 mL) was treated with 1-hydroxybenzotriazole (162 mg, 1.2 mmole), EDC (230 mg, 1.2 mmole), and D-Boc-phenylalanine (318 mg, 1.2 mmole). The reaction was stirred at room temperature for 1 hr and poured into saturated sodiumbicarbonate (125 mL). The aqueous mixture was extracted with ethyl acetate (3×100 mL). The combined organics were dried over anhydrous magnesium sulfate, filtered and concentrated at reduced pressure to give the crude product. The material thus obtained was dissolved in ethyl acetate (100 mL), cooled to 0° C. and treated with excess gaseous HCl for 15 minutes. The reaction was warmed to room temperature and poured into saturated sodiumbicarbonate (200 mL) and 1 N NaOH (30 mL). The aqueous mixture was extracted with ethyl acetate (3×100 mL). The combined organics were dried over anhydrous magnesium sulfate, filtered and concentrated at reduced pressure to give the crude mixture of diastereomers. The material thus obtained was chromatographed on silica gel eluting with 3%MeOH / chloroform to give the two diastereomers designated as alpha (faster running, 210 mg) and Beta( slower running, 195 mg). Each isomer was carded through the following sequence seperately but is described only for the alpha isomer. The Higher Rf material (alpha) was dissolved in methylene chloride (2 mL) and treated with phenylisothiocyanate (64 mg, 0.47 mmole) and warmed to 40° C. for 30 minutes. Trifluoroacetic acid (0.5 mL) was added and the reaction heated to 50° C. for 30 minutes. The reaction was cooled to room temperature and poured into ethyl acetate (50 mL). The product was extracted into 1 N HCl(3×50 mL). The combined aqueous extracts were adjusted to pH of 8 with 1 N NaOH and saturated sodiumbicarbonate (100 mL). The aqueous mixture was extracted with ethyl acetate (3×50 mL). The combined organics were dried over anhydrous magnesium sulfate, filtered and concentrated at reduced pressure to give the crude amine as a single enantiomer. The material thus obtained was dissolved in methylene chloride (10 mL) and treated with acetic anhydride (0.15 mL)) and triethylamine (0.15 mL) at room temperature. The reaction was poured into saturated sodiumbicarbonate (125 mL). The aqueous mixture was extracted with ethyl acetate (3×50 mL). The combined organics were dried over anhydrous magnesium sulfate, filtered and concentrated at reduced pressure. The residue was chromatographed on silica gel eluting with 4% MeOH / chloroform to give pure (−)-(4S)-4-Acetamido-1'-[2-(4-cyanophenyl)ethyl]-3,4-dihydro-6-methoxyspiro(2H-1-benzopyran-2,4'-piperidine). The free base was treated with excess ethanolic HCl to generate the hydrochloride.

$[\alpha]_D = -55.7\ (C=0.43,\ \text{MeOH})$

EXAMPLE 9

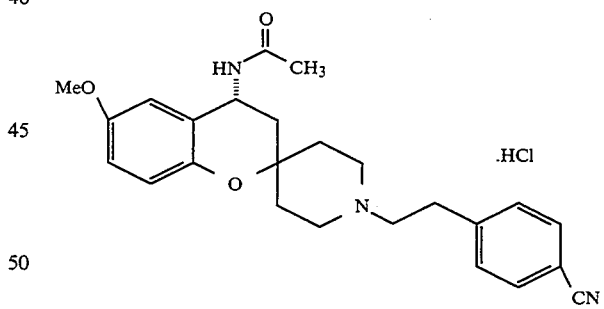

(+)-(4R)-4-Acetamido-1'-[2-(4-cyanophenyl)ethyl]-3,4-dihydro-6-methoxyspiro(2H -1-benzopyran-2,4'-piperidine) hydrochloride.

Prepared in a manner substantially as described above for (−)-(4S)-4-Acetamido-1'-[2-(4-cyanophenyl) ethyl]-3,4-dihydro-6-methoxyspiro(2H- 1-benzopyran-2,4'-piperidine) hydrochloride.

SCHEME IV

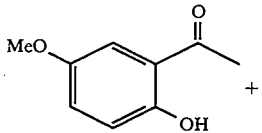

17

-continued
SCHEME IV

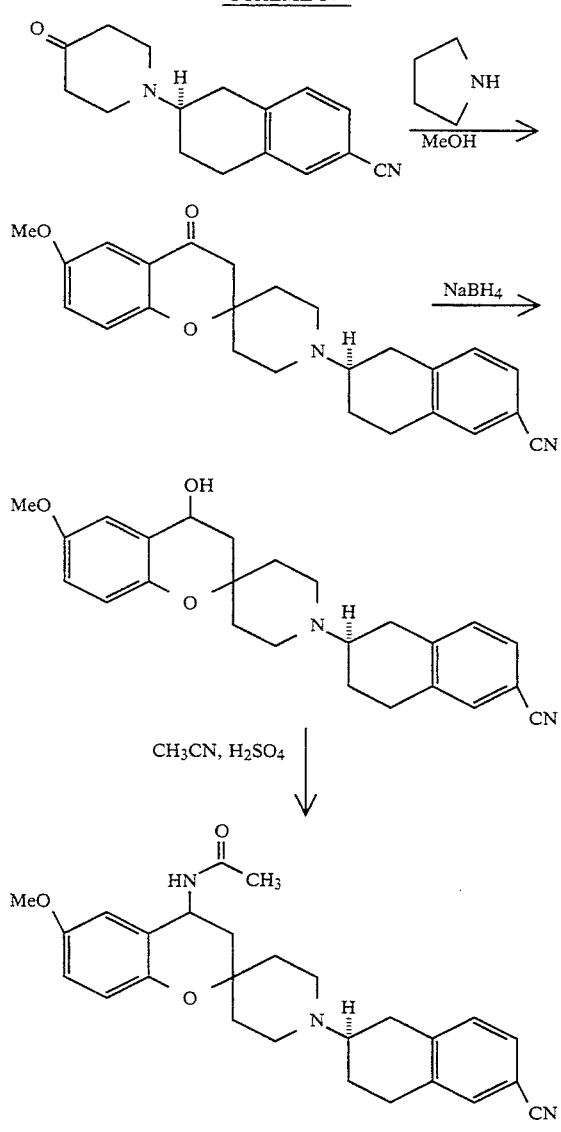

EXAMPLE 10

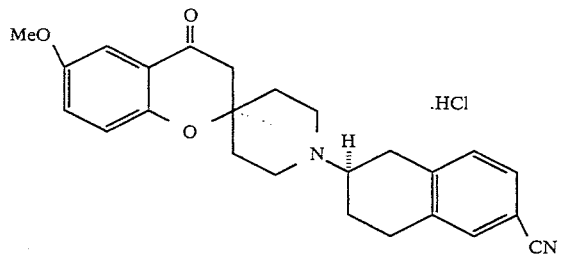

(+)-(2″R)-1′-(6-Cyano-1,2,3,4-tetrahydronaphthalen-2-yl)-3,4-dihydro-6-methoxyspiro (2H-1-benzopyran-2,4′-piperidine)-4-one hydrochloride A solution of 5′-methoxy-2′-hydroxyacetophenone (8.5 g, 51.16 mmol) in methanol (400 ml) at room temperature was treated with pyrrolidine (3.63 g, 51.16 mmol). The reaction was stirred at room temperature for 5 min., (2′R)-N-(6-cyano-1′,2′,3′,4′-tetrahydonapthalen-2-yl)piperidine -4-one (10 g, 39.3 mmol) was added and the reaction stirred at ambient temperature for 18 h. The reaction was concentrated at reduced pressure and the residue was partitioned between ethyl acetate (500 ml) and saturated sodium bicarbonate (500 ml). The layers were separated and the aqueous phase was extracted with two additional 300 ml portions of ethyl acetate. The combined extracts were dried over anhydrous magnesium sulfate, filtered, and concentrated at reduced pressure. The residue was chromatographed on silica gel with chloroform/methanol (98:2 to 90:10) as eluent to give 9.3 g of free base. A 200 mg sample of this material was treated with excess ethanolic HCl and the product crystallized from ethanol to give the hydrochloride (132 mg, 36%), m.p. 270°-272 ° C., $[\alpha]_D = +44.6°$ (c=0.3, MeOH).

Elementary analysis for $C_{25}H_{26}N_2O_3.HCl.H_2O$:

Calculated; C 65.70; H 6.40; N 6.41%. Found; C 65.95; H 6.14; N 6.29%.

EXAMPLE 11

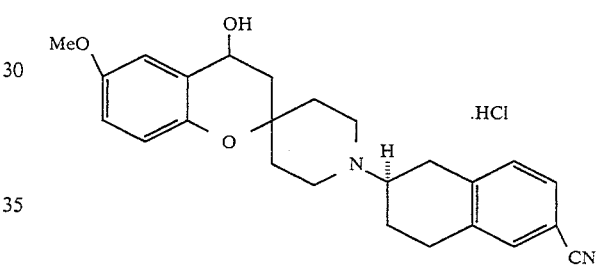

(4RS, 2″R)-1′-(6-Cyano-1,2,3,4-tetrahydronaphthalen-2-yl)-3,4-dihydro-6-methoxyspiro(2H-1-benzopyran-2,4′-piperidine)-4-ol hydrochloride A solution of (+)-(2″R)-1′-(6-Cyano-1,2,3,4-tetrahydronaphthalen-2-yl)-3,4-dihydro-6-methoxyspiro(2H-1-benzopyran-2,4′-piperidine)-4-one (1.2 g, 3 mmol) in ethanol (100 ml) at room temperature was treated with sodium borohydride (0.22 g, 5.8 mmol) and stirred at room temperature for 1 h. The reaction was poured into saturated aqueous sodium bicarbonate (300 ml) and extracted with ethyl acetate (3×200 ml). The combined extracts were dried over anhydrous magnesium sulfate, filtered, and concentrated at reduced pressure. The residue was chromatographed on silica gel with chloroform/methanol (98:2 to 90:10) as eluent to give 0.98 g of free base. A 180 mg sample of the material thus obtained was treated with excess ethanolic HCl and the product crystallized from ethanol to give the hydrochloride (140 mg, 58%), m.p. 265°-267 ° C.

Elementary analysis for $C_{25}H_{28}N_2O_3.HCl.0.45EtOH$:

Calculated; C 67.37; H 6.92; N 6.07%. Found; C 67.70; H 6.93; N 5.98%.

EXAMPLE 12

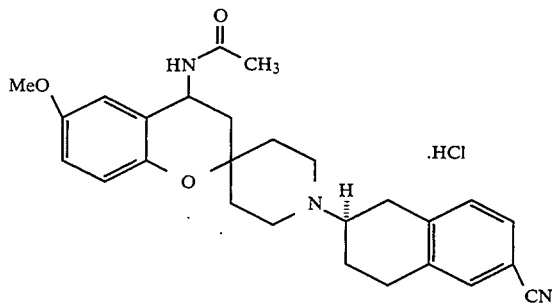

(4RS, 2″R)-4-Acetamido-1′-(6-cyano-1,2,3,4-tetrahydronaphthalen-2-yl)-3,4-dihydro-6-methoxyspiro(2H-1-benzopyran-2,4′-piperidine) hydrochloride A solution of (4RS, 2″R)-1′-(6-cyano-1,2,3,4-tetrahydronaphthalen-2-yl)-3,4-dihydro-6-methoxyspiro(2H1-benzopyran-2,4′-piperidine)-4-ol (800 mg, 1.98 mmol) in acetonitrile at room temperature was treated with concentrated sulfuric acid (0.27ml) and the reaction stirred at room temperature for 2 h. The reaction was poured into saturated aqueous sodium bicarbonate (300 ml) and extracted with ethyl acetate (3×200 ml). The combined extracts were dried over anhydrous magnesium sulfate, filtered, and concentrated at reduced pressure. The residue was chromatographed on silica gel with chloroform/methanol (97:3 to 93:7) as eluent to give 0.522 g of free base. This material was treated with excess ethanolic HCl and the product crystallized from ethanol to give the hydrochloride (303 mg, 32%), m.p. >315 ℃.

Elementary analysis for $C_{27}H_{31}N_3O_3.HCl.0.60H_2O$:

Calculated; C 65.80; H 6.79; N 8.53%. Found; C 65.78; H 6.56; N 8.60%.

SCHEME V

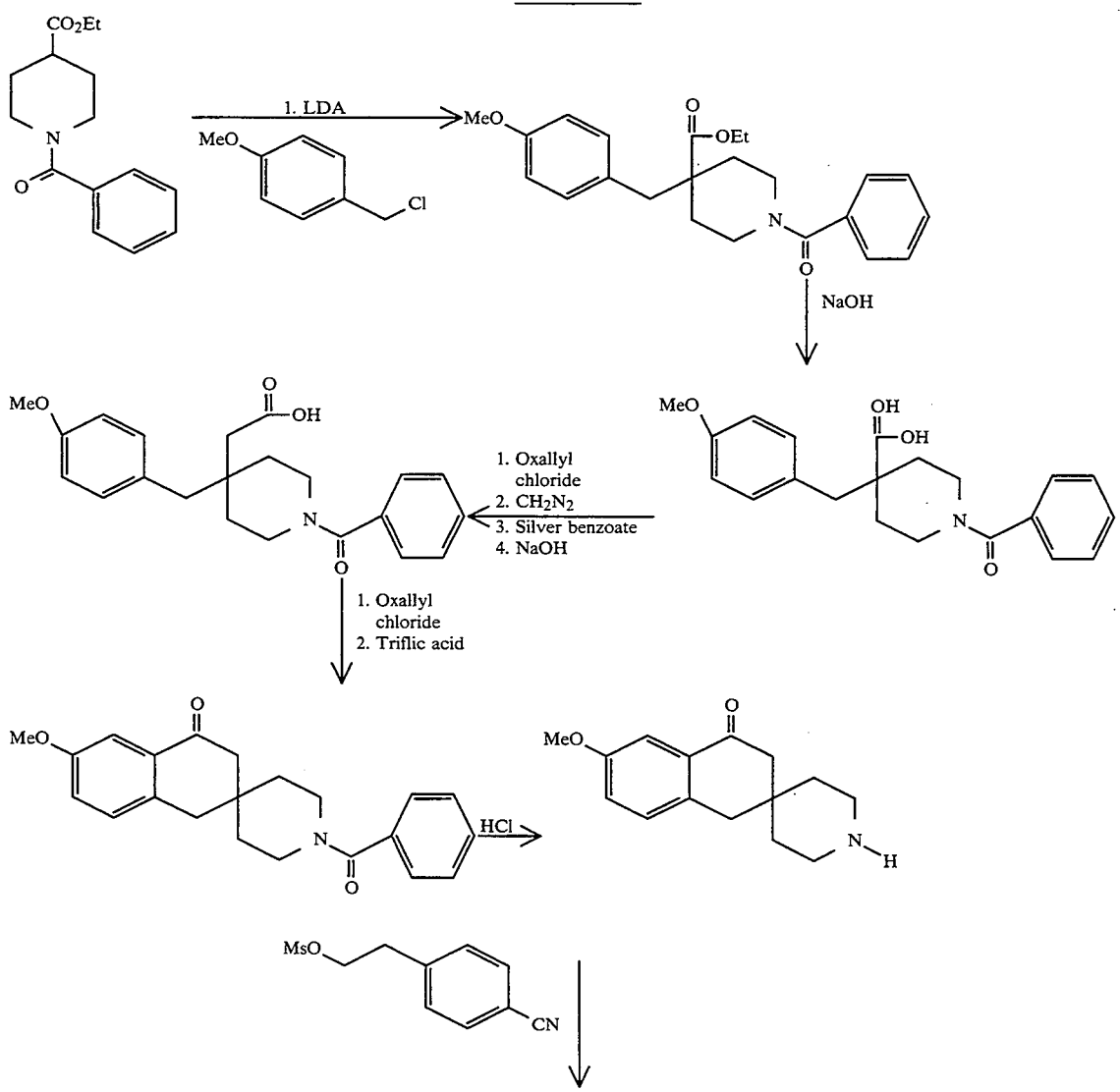

-continued
SCHEME V

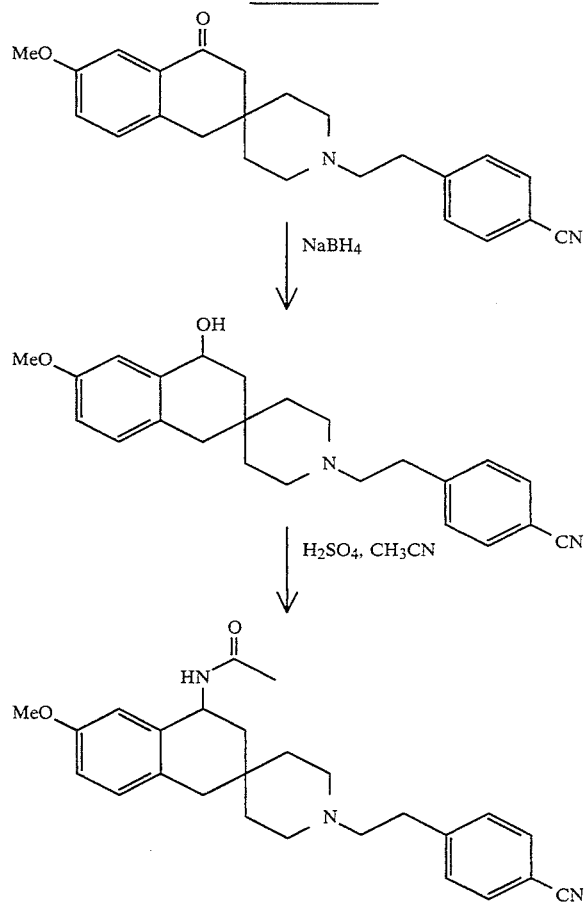

EXAMPLE 13

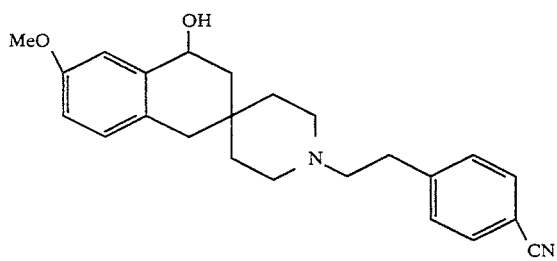

1'-[2-(p-cyanophenyl)ethyl]3,4-dihydro-7-[(methoxy)]spiro-[naphthalene-3,4'-piperidine]-1-ol

Step A

Preparation of 4 - (4-methoxybenzyl)-N-benzoylisonipecotic acid

A solution of ethyl-N-benzoylisonipecotate (52 g, 0.2 mole) in THF (1 L) at −78° C. is treated with a solution of LDA in THF (110 mL of a 1 M solution). The solution is stirred at −78° for 15 minutes at which time 4-methoxybenzyl chloride (37.5 g, 0.22 moles) is added and the reaction warmed to room temperature over 2 hours. The reaction is concentrated at reduced pressure to @ one quarter volume and then poured into saturated aqueous sodium bicarbonate (1 L) and extracted with ethyl acetate (3×500 mL). The combined extracts were dried over anhydrous magnesium sulfate, filtered, and concentrated at reduced pressure. The residue is chromatographed on silica gel with 30% ethyl acetate / hexane as eluent to give 66 g. The material thus obtained is dissolved in isopropyl alcohol (150 mL) and THF (150 mL) and treated with 10 N NaOH (250 mL). The mixture is heated to reflux for 48 hr. The reaction is cooled to room temperature and carefully neutralized by pouring over 1 L of crushed ice and adding 6 N HCl until pH 3. The mixture is then extracted with ethyl acetate (3×500 mL). The combined extracts were dried over anhydrous magnesium sulfate, filtered, and concentrated at reduced pressure to give the product.

Step B

N-benzoyl-4-methoxybenzyl-4-methoycarbonylmethylpiperidine

A solution of 4-methoxybenzyl-N-benzoylisonipecotic acid (10 g, 0.030 moles) in methylene chloride (250 mL) at room temperature is treated with N,N-dimethylformamide (0.2 mL). Oxallyl chloride (3.93 g, 2.70 mL, 0.031 mole) is then added slowly over 5 minutes. The reaction is stirred at room temperature for 1 hour and then concentrated in vacuo to give the crude acid chloride which is dried under vacuum overnight. A portion of the crude acid chloride (5.6 g, 0.016 mole)) is dissolved in THF (50 mL) and treated with a solution of diazomethane in ether [prepared by adding N-methyl-N nitroso-N'-nitroguanidine (7.2 g, 0.048 mole, 3 equiv.) to a flask containing 100 mL of 10% KOH and 200 mL of ether at 0° C., and decanting the upper ether layer]. The reaction is allowed to stand at room temperature overnight and then treated with a few drops of acetic acid to decompose any excess diazomethane. The reaction is then concentrated at reduced pressure to give the crude diazoketone. This material is dissolved in methanol (50 mL) and treated with a solution of silver benzoate (300 mg) in trietylamine (2 mL). After stirring for 1 hour at room temperature the reaction is poured into saturated aqueous sodium bicarbonate and extracted with ethyl acetate (2×200 mL). The combined extracts were dried over anhydrous magnesium sulfate, filtered, and concentrated at reduced pressure. The residue is chromatographed on silica gel with 30% ethyl acetate / hexane as eluent to give the product (contaminated with approximately 15% of the non-homologated methyl ester).

Step C

Preparation of N-Benzoyl-3,4-dihydro-7-methoxyspiro-[naphthalene-3,4'-piperidine]-1-one The material obtained from step 2 above is dissolved in THF (50 mL) and methanol (20 mL) treated with 1 N NaOH (100 mL). The reaction is stirred at room temperature for 1 hour, diluted with water (300 mL) and extracted with ether (2×100 mL). The ether layers were discarded and the aqueous phase acidified to pH 2 with 6 N HCl and extracted with ethyl acetate (3×200 mL). The combined extracts were dried over anhydrous magnesium sulfate, filtered, and concentrated at reduced pressure to give the crude acid. The material thus obtained is dissolved in methylene chloride and treated with DMF (0.1 mL) and then oxallyl chloride (1.32 g, 10.4 mmole, 0.91 mL). The reaction is allowed to stir at room temperature for 1 hour and then treated with trifluoromethane sulfonic acid (4.23 g, 28.2 mmole, 2.5 mL). After stirring for 1 hour at room temperature the reaction is poured into saturated aqueous sodium bicarbonate (300 mL) and extracted with ethyl acetate( 3×200 mL). The combined extracts were dried over anhydrous magnesium sulfate, filtered, and concentrated at reduced pressure to give the product.

Step D

Preparation of 3,4-dihydro-7-methoxyspiro-[naphthalene-3,4'-piperidine]-1-one hydrochloride A solution of N-Benzoyl-3,4-dihydro-7-methoxyspiro-[naphthalene-3,4'-piperidine]-1-one (3.4 g, 7.8 mmole) in ethanol (100 mL) is treated with 6 N HCl (100 mL) and heated to reflux for 5 hours. The reaction is cooled to 90° C. and heated at this temperature for 16 hours. The reaction is cooled to room temperature, diluted with 300 mL water and extracted with two 75 mL portions of ethyl acetate. The aqueous phase is then diluted with ethanol (1 L) and concentrated at reduced pressure to dryness. The residue is crystallized from ethanol (100 mL) to give the product as the hydrochloride.

Step E

1'-[2-(p-cyanophenyl)ethyl]3,4-dihydro-7-[(methoxy]spiro-[naphthalene-3,4'-piperidine]-1-one hydrochloride A 100 mL round bottom flask is charged with 3,4-dihydro-7-methoxyspiro-[naphthalene-3,4'-piperidine]-1 -one hydrochloride from step 6 above (1.38g, 4 mmole), p-cyanophenyl ethyl mesylate (1 g, 4.44 mmole), solid sodium bicarbonate (740 mg, 8.8 mmole), and acetonitrile (50 mL) and the mixture is heated to reflux for 24 hours. The reaction is cooled to room temperature and poured into saturated aqueous sodium bicarbonate (300 mL) and extracted with ethyl acetate (3×300 mL). The combined extracts were dried over lo anhydrous magnesium sulfate, filtered, and concentrated at reduced pressure. The residue is chromatographed on silica gel with chloroform/methanol (95:5) as eluent to give 1.52 g of free base. A portion of the material thus obtained (150 mg) is treated with excess ethanolic HCl and the product crystallized from ethanol to give the hydrochloride.

STEP F

1'-[2-(p-cyanophenyl)ethyl]3,4-dihydro-7-[(methoxy]spiro-[naphthalene-3,4'-piperidine]-1-ol A solution of 1'-[2-(p-cyanophenyl)ethyl]3,4-dihydro-7-[(methoxy]spiro-[naphthalene-3,4'-piperidine]-1-one (200 mg, 0.46 mmol) in ethanol (15 ml) at room temperature is treated with sodium borohydride (0.35 g, 0.92 mmol) and stirred at room temperature for 1 h. The reaction is poured into saturated aqueous sodium bicarbonate and extracted with ethyl acetate. The combined extracts were dried over anhydrous magnesium sulfate, filtered, and concentrated at reduced pressure. The residue is chromatographed on silica gel with chloroform/methanol (95:5) as eluent to give 0.160 g of free base. The material thus obtained is treated with excess ethanolic HCl and the product crystallized from ethanol to give the hydrochloride.

EXAMPLE 14

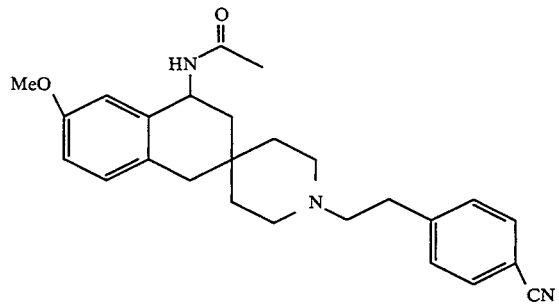

1-(RS)-1-Acetamido-1'-[2-(p-cyanophenyl)ethyl]3,4-dihydro-7-methoxyspironaphthalene -3,4'-piperidine A solution of 1'-[2-(p-cyanophenyl)ethyl]3,4-dihydro-7-[(methoxy]spiro-[naphthalene-3,4'-piperidine]-1-ol (100 mg, 0.23 mmol) in acetonitrile (5 mL) at room temperature is treated with concentrated sulfuric acid (0.25 ml) and the reaction stirred at room temperature for 2 h. The reaction is poured into saturated aqueous sodium bicarbonate (300 ml) and extracted with ethyl acetate (3×100 ml). The combined extracts were dried over anhydrous magnesium sulfate, filtered, and concentrated at reduced pressure. The residue is chromatographed on silica gel with chloroform/methanol (97:3 to 95:5) as eluent to give the free base. This material is treated with excess ethanolic HCl and the product crystallized from ethanol to give the hydrochloride.

SCHEME VI
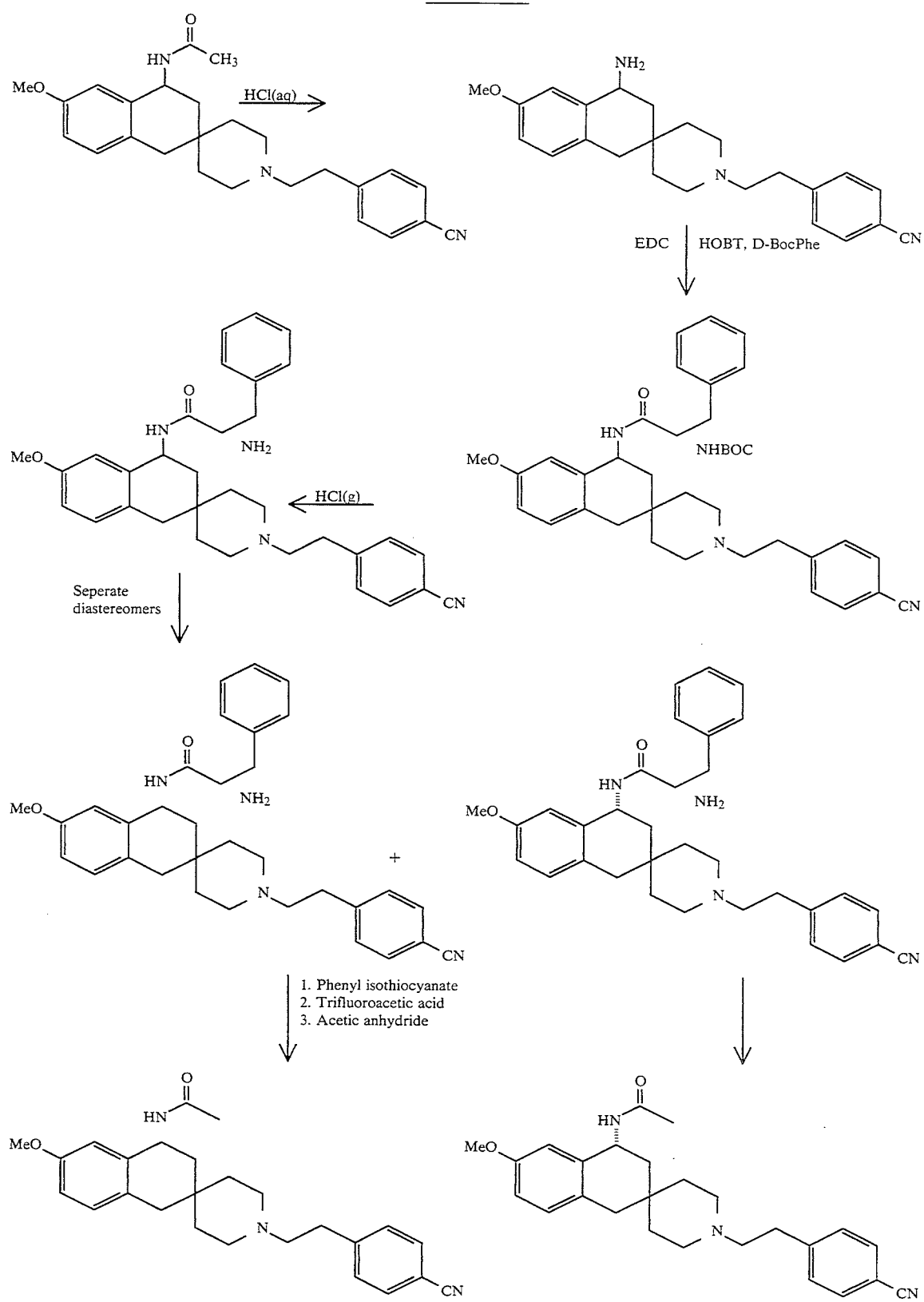

EXAMPLE 15

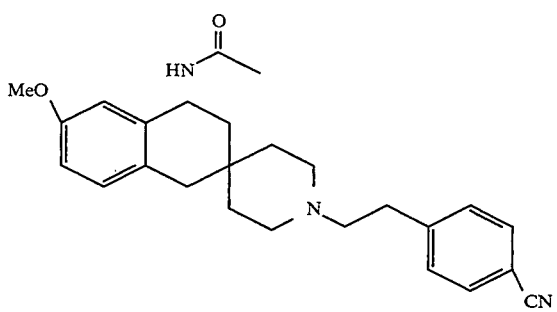

(1S)-1-Acetamido-1'-[2-(p-cyanophenyl)ethyl]3,4-dihydro-7-methoxyspironaphthalene-3,4'-piperidine Prepared from the product of example 14 in a manner substantially as described above as described above for the preparation of Example 8. See Scheme 6

EXAMPLE 16

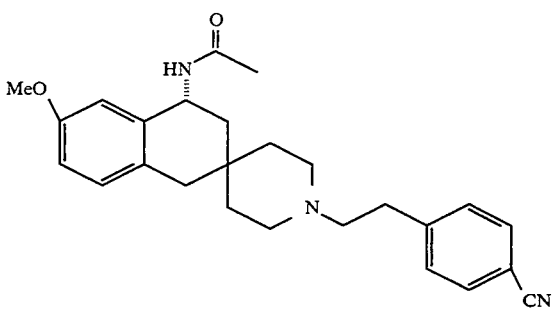

(1R)-1-Acetamido-1'-[2-(p-cyanophenyl)ethyl]-3,4-dihydro-7-methoxyspironaphthalene-3,4'-piperidine Prepared from the product of example 14 in a manner substantially as described above for the preparation of Example 9. See Scheme 6.

EXAMPLE 17

IN VITRO TEST FOR CLASS III ANTIARRHYTHMIC ACTIVITY PURPOSE

This in vitro assay is designed to assess possible potassium channel blocking activity of a compound based on its ability to prolong effective refractory period (ERP) in isolated papillary muscle.

TISSUE PREPARATION

Ferrets (700 to 1200 grams) are anesthetized with 0.7 mL of a mixture of xylazine and ketamine HCL in 1:7 ratio. Papillary muscles from the right ventricle are quickly excised from the isolated heart and mounted in 50 mL organ baths containing Krebs-Henseleit solution (pH=7.2-7.4) at 37—° C. The composition of the solution in millimoles per liter are as follows: NaCl, 118; KCl, 4.7; $Na_2CO_3$, 23; $CaCl_2.2H_2O$, 2; $MgSO_4.7H_2O$, 1.2; $KH_2PO_4$, 1.2; Dextrose, 11.1. Timolol ($10^{-7}M$) is added to the solution to block the effects of released catecholamines during stimulation of the muscles. This solution is aerated with 95% $O_2$ and 5% $CO_2$. The tissue is stimulated at 1 Hz at one msec pulse duration by a square wave stimulator at a voltage 30% above the threshold through platinum electrodes that touch the tissue just above the bottom attachment point. The tendenous end of the tissue is connected by thread to an isometric force transducer leading to a polygraph.

EFFECTIVE REFRACTORY PERIOD (ERP) MEASUREMENT

The ERP is determined by a standard 2 pulse protocol. Both pulses are stimulated at 1.3 x voltage threshold. While pacing the tissue at a basal frequency of 1 Hz, a single extra stimulus is delivered after a variable time delay. The shortest delay resulting in a propagated response is defined as the ERP.

PROTOCOL

1. Tissues are mounted with a resting tension of 0.5 gms, stimulated at 1 Hz, and allowed to equilibrate for 2 hours with washings at 15–20 minute intervals.

2. Voltage is adjusted to 30% above threshold and resting tension is adjusted for maximum developed reequilibration time.

3. Effective refractory period is measured at 1 Hz. Changes in resting tension and developed force are noted.

4. After equilibration, ERP's and developed force are measured at 30 minutes following the addition of increasing cumulative concentrations for test agent to the organ bath. Four to five concentrations of test agents were used to generate a concentration-response curve.

5. Four tissues per compound are tested.

RESULTS

Employing the above protocol, it has been found that the effective concentration of most of the compounds of this invention required to increase the refractory period by an increment of 25% above baseline is less than or equal to 10 micromolar, i.e. $EC_{25}$ less than or equal to 10 micromolar, whereas sotalol in the same protocol has an $EC_{25}$ of approximately 20 micromolar.

EXAMPLE 18

PREPARATION OF INTRAVENOUS SOLUTIONS

A solution containing 0.5 mg of active ingredient per mL of injectable solution is prepared in the following manner:

A mixture of 0.5 mg of active ingredient is dissolved in 1 mL of acetate buffer. The pH is adjusted using hydrochloric acid or aqueous sodium hydroxide to about pH 5.5. If it is desired that the intravenous solution be used for multi-dose purposes, 1.0 mg of methyl-p-hydroxy benzoate (methyl paraben) and 0.10 mg of n-propyl-p-hydroxy benzoate (propyl paraben) are mixed with the other solids before adding water to dissolve the solids. The solution is prepared and stored in such a manner that it is suitably protected from the deleterious effects of the atmosphere. One method by which this can be accomplished is by preparation and storage of the solution in an atmosphere of nitrogen. The resulting solution is sterilized by autoclaving. Injectable solutions comprising 0.001, 0.01 and 0.1 mg, respectively, of active ingredient per mL of solution are similarly prepared substituting the indicated amount for the above-illustrated 10 mg quantity. Bulk injectable solutions of convenient volume for subsequent delivery in unit dosage form are readily prepared following the above procedure.

EXAMPLE 19

TABLET PREPARATION

Tablets containing 1.0, 2.0, 25, 26.0, 50.0 and 100.0 mg, respectively, of active ingredient are prepared as illustrated below.

| TABLE FOR DOSES CONTAINING FROM 1-25 mg OF THE ACTIVE COMPOUND | | | |
|---|---|---|---|
| | Amount in mg | | |
| Active ingredient | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 mg OF THE ACTIVE COMPOUND | | | |
|---|---|---|---|
| | Amount in mg | | |
| Active ingredient | 26.0 | 50.0 | 100.0 |
| Microcrystalline cellulose | 25.0 | 100.0 | 200.0 |
| Modified food corn starch | 0.39 | 4.25 | 8.5 |
| Magnesium stearate | 0.39 | 0.75 | 1.50 |

All of the active compound, cellulose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50 mg, and 100 mg of active ingredient per tablet.

The compounds of this invention provide sustained biological activity over other similar compounds in their class. That is, these compounds provide antiarrhythmic activity when delivered to animals, including humans, for time periods in excess of 12 hours.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of the structural formula:

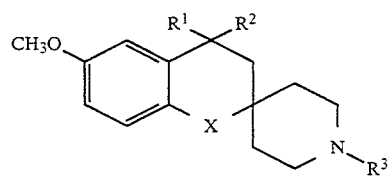

wherein:
$X$ is $CH_2$;
$R^1$ is H if $R^2$ is not H or if $R^2$ is H then $R^1$ is

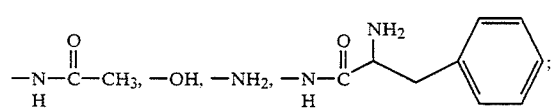

$R^2$ is —H if $R^1$ is not H or if $R^1$ is H then $R^2$ is

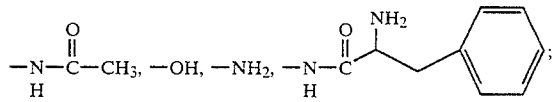

and $R^3$ is

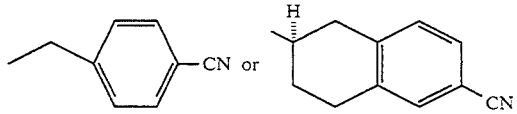

or a pharmaceutically acceptable salt, hydrate or crystal form thereof.

2. The compound of claim 1 selected from the group consisting of

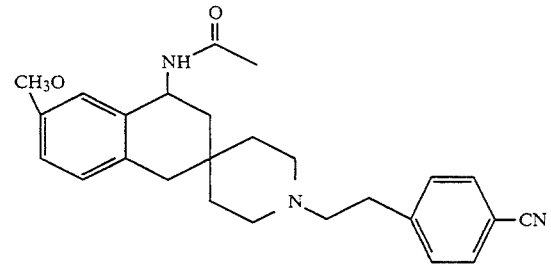

1-(RS)-1-Acetamido-1'-[2-(p-cyanophenyl)ethyl]3,4-dihydro-7-methoxyspironaphthalene -3,4'-piperidine;

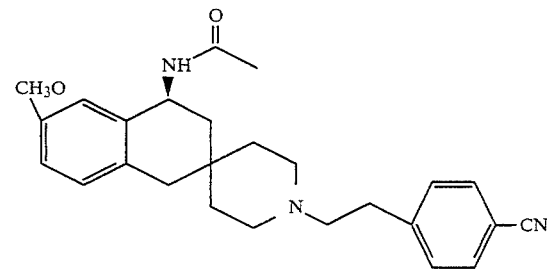

(1S)-1-Acetamido-1'-[2-(p-cyanophenyl)ethyl]3,4-dihydro-7-methoxyspironaphthalene -3,4'-piperidine; or

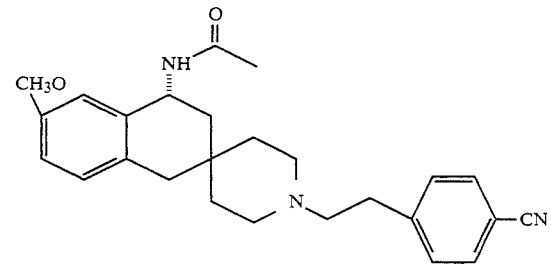

3. A pharmaceutical formulation comprising a carrier and an amount of a compound of claim 1 which is therapeutically effective for the treatment of arrhythmia for those in need thereof.

4. The pharmaceutical formulation of claim 3, wherein the pharmaceutically effective amount of compound ranges from about 1.0 mg to about 100 mg of the compound.

5. The pharmaceutical formulation of claim 3, which comprises from about compound ranges from about 2.0 mg to about 25 mg of the compound.

6. A method of treating arrhythmia and/or impaired cardiac pump function in a patient in need of such treatment which comprises administering to such patient a therapeutically effective amount of the compound of claim 1.

7. The method of claim 6 wherein the therapeutically effective amount of compound is administered orally or intravenously.

8. The pharmaceutical formulation of claim 3 wherein the formulation is compressed into a tablet which comprises from about 1.0 mg to about 100 mg of the compound.

9. The pharmaceutical formulation of claim 3, wherein the formulation is compressed into a tablet which comprises from about 2.0 mg to about 25 mg of the compound.

* * * * *